(12) United States Patent
Kofoed et al.

(10) Patent No.: US 9,040,660 B2
(45) Date of Patent: May 26, 2015

(54) LONG-ACTING GASTRIN DERIVATIVES

(75) Inventors: Jacob Kofoed, Vaerloese (DK); Carsten Engaard Stidsen, Soeborg (DK); Frantisek Hubalek, Herlev (DK); Flemming S. Nielsen, Roskilde (DK); Henning Thoegersen, Farum (DK); Johannes Fels, Slangerup (DK); Rikke Bjerring Andersen, Koebenhavn V (DK); Janos Tibor Kodra, Koebenhavn Oe (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/642,184

(22) PCT Filed: Apr. 19, 2011

(86) PCT No.: PCT/EP2011/056197
§ 371 (c)(1),
(2), (4) Date: Nov. 20, 2012

(87) PCT Pub. No.: WO2011/131646
PCT Pub. Date: Oct. 27, 2011

(65) Prior Publication Data
US 2013/0059781 A1    Mar. 7, 2013

Related U.S. Application Data

(60) Provisional application No. 61/327,381, filed on Apr. 23, 2010.

(30) Foreign Application Priority Data

Apr. 20, 2010 (EP) .................................. 10160402

(51) Int. Cl.
| C07K 14/595 | (2006.01) |
| A61K 38/22 | (2006.01) |
| C07K 14/00 | (2006.01) |
| A61K 38/00 | (2006.01) |

(52) U.S. Cl.
CPC ............... *C07K 14/595* (2013.01); *A61K 38/00* (2013.01); *A61K 38/22* (2013.01); *A61K 38/2207* (2013.01); *C07K 14/00* (2013.01)

(58) Field of Classification Search
CPC ... A61K 38/00; A61K 38/22; A61K 28/2207; C07K 14/595; C07K 14/00
See application file for complete search history.

(56) References Cited

U.S. PATENT DOCUMENTS

| 5,837,218 | A | * | 11/1998 | Peers et al. .................... 424/1.69 |
| 2004/0266682 | A1 | * | 12/2004 | Cruz ................................ 514/12 |
| 2008/0039379 | A1 | | 2/2008 | Cruz |
| 2008/0051557 | A1 | | 2/2008 | Bachovchin et al. |
| 2009/0111730 | A1 | | 4/2009 | Dorwald et al. |

FOREIGN PATENT DOCUMENTS

| WO | 02/10195 A2 | 2/2002 | |
| WO | 02/055152 | 7/2002 | |
| WO | 02098446 A1 | 12/2002 | |
| WO | 2005/027978 | 3/2005 | |
| WO | 2005/028516 A2 | 3/2005 | |
| WO | 2009/030771 A1 | 3/2009 | |
| WO | WO 2009/030738 A1 * | 3/2009 | ........... C07K 14/605 |
| WO | WO 2009/083549 A1 * | 7/2009 | ............... C07K 1/10 |

OTHER PUBLICATIONS

Yamamoto, Improvement of Intestinal Absorption of Peptide and Protein Drugs by Chemical Modification with Fatty Acids, Japanese Journal of Clinical Medicine, 1998, 55, pp. 49-55.*
English translation of Yamamoto, Improvement of Intestinal Absorption of Peptide and Protein Drugs by Chemical Modification with Fatty Acids, Japanese Journal of Clinical Medicine, 1998, 55, enclosed pp. 1-18.*
Needleman et al., "A General Method Applicable to the Search for Similarities in the Amino Acid Sequence of Two Proteins", Journal of Molecular Biology, 1970, vol. 48, p. 443-453.
Rooman et al., "Gastrin Stimulates β-Cell Neogenesis and Increases Islet Mass From Transdifferentiated But Not From Normal Exocrine Pancreas Tissue", Diabetes, 2002, vol. 51, p. 687-690.
Meier et al., "Increased Islet Beta Cell Replication Adjacent to Intrapancreatic Gastrinomas in Humans", Diabetologia, 2006, vol. 49, p. 2689-2696.
Rooman et al., "Combined Gastrin and Epidermal Growth Factor Treatment Induces Islet Regeneration and Restores Normoglycaemia in C57BI6/J Mice Treated With Alloxan", Diabetologia, 2004, Vol. 47, pp. 259-265.
Sampson et al., "The Synthesis of 'Difficult' Peptides Using 2-Hydroxy-4-Methoxybenzyl or Pseudoproline Amino Acid Building Blocks: A Comparative Study", Journal of Peptide Science, 1999, vol. 5, pp. 403-409.
Walsh, "Circulating Gastrin", Annual Review of Physiology, 1975, vol. 37, pp. 81-104.
Myers and Miller, "Optimal Alignments in Linear Space", CABIOS: Computer Applications in Biosciences, 1988, vol. 4, pp. 11-17.
Wilma L et al, Journal Title: Diabetes,Title: Combination Therapy With Glucagon-Like Peptide-1 and Gastrin Restores Normoglycemia in Diabetic NOD Mice,Year: 2008, vol. 57, pp. 3281-3288.

* cited by examiner

*Primary Examiner* — Julie Ha
*Assistant Examiner* — Li Ni Komatsu
(74) *Attorney, Agent, or Firm* — Nonna G. Akopyan; Reza Green; Richard W. Bork

(57) ABSTRACT

The present invention relates to gastrin derivatives comprising gastrin or an analogue or fragment thereof and a derivatisation group and therapeutic use thereof.

3 Claims, No Drawings

LONG-ACTING GASTRIN DERIVATIVES

CROSS-REFERENCE TO RELATED APPLICATIONS

This application is a 35 U.S.C. §371 national stage application of International Patent Application PCT/EP2011/056197 (published as WO 2011/131646 A1), filed Apr. 19, 2011, which claimed priority of European Patent Application 10160402.3, filed Apr. 20, 2010; this application further claims priority under 35 U.S.C. §119 of U.S. Provisional Application 61/327,381, filed Apr. 23, 2010.

FIELD OF THE INVENTION

The present invention relates to the field of therapeutic peptides, in particular long-acting gastrin derivatives comprising gastrin or an analogue or fragment thereof and a derivatisation group as well as therapeutic use thereof.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Sep. 12, 2012. The Sequence Listing is made up of 1,327 bytes, and the information contained in the attached "SEQUENCE LISTING" is identical to the information in the specification as originally filed. No new matter is added.

BACKGROUND OF THE INVENTION

Gastrin and analogues hereof (either alone or in combination with EGF or GLP-1) have been shown in animal models as well as in human clinical trials to improve both type 1 and type 2 diabetes via stimulation of beta cell proliferation and thereby increasing native insulin production. Several forms of gastrin are found in circulation, for example, gastrin-34, gastrin-17, gastrin-14, etc. Gastrin-17, one of the most abundant form of gastrin, is however, rapidly cleared from circulations; the half life is 2-8 min for human gastrin in dogs and man. Accordingly, long-acting gastrin analogues are desirable and would have a clear advantage in clinical use of gastrin by eliminating frequent injections.

SUMMARY OF THE INVENTION

In one embodiment the invention relates to a gastrin derivative comprising gastrin or an analogue or fragment thereof and a derivatisation group. In one embodiment the invention relates to a gastrin derivative comprising gastrin or an analogue or fragment thereof and a derivatisation group, wherein said derivatisation group is attached to a position selected from the group consisting of the N-terminal amino group, position 2, 3, 4, 5, 6, 7, 8, 9, 10 or 11, such as the group consisting of the N-terminal amino group, position 2, 3, 4, 5, 6, 7 or 8 or the group consisting of position 2 and position 3, wherein said positions correspond to gastrin-17.

In one embodiment the invention relates to the gastrin derivative as defined herein for use in medicine. In one embodiment the invention relates to the gastrin derivative as defined herein for the stimulation of beta cell proliferation, treatment of or reduction of symptoms associated with type 1 diabetes or type 2 diabetes, or treatment of diabetes, hypertension, chronic heart failure, fluid retentive states, obesity or metabolic syndrome.

DESCRIPTION OF THE INVENTION

In one embodiment the gastrin derivatives of the invention have a longer half life compared to human gastrin-17. In one embodiment the gastrin derivatives of the invention have a longer mean residence time in plasma.

Gastrin

In one embodiment the invention relates to a gastrin derivative comprising a gastrin or an analogue or fragment thereof and a derivatisation group. In one embodiment gastrin is derived from the group consisting of big gastrin, little gastrin, mini gastrin, N-terminally truncated gastrin and analogues thereof. In one embodiment origin of the gastrin is selected from the group consisting of human, pig, mouse, dog, rat, cow, cat, horse, sheep, goat, kangaroo and chinchilla.

In one embodiment the gastrin derivative comprises gastrin selected from the group consisting of gastrin-34, gastrin-17 and gastrin-14. In one embodiment human gastrin-34 and human gastrin-17 comprises a modification of Q in position 1 into pyrrolidone carboxylic acid, i.e. pyroglutamic acid. In one embodiment human gastrin-34, and human gastrin-17 and human gastrin-14 comprises a modification of the C-terminal F into phenylalanine amide.

The terms "big gastrin" and "gastrin-34" are used interchangeably herein. In one embodiment the term "gastrin-34" is intended to mean the analogue of human gastrin-34 which is defined by the amino acid sequence QLGPQGPPHL VADPSKKQGP WLEEEEEAYG WMDF, wherein the C-terminal carboxylic acid of F is converted into an amide (SEQ ID NO: 1). In one embodiment gastrin-34 has GenPept accession no. CAA25006.

The terms "little gastrin" and "gastrin-17" are used interchangeably herein. In one embodiment the term "gastrin-17" is intended to mean the analogue of human gastrin-17 which is defined by the amino acid sequence QGPWLEEEEE AYG-WMDF, wherein the C-terminal carboxylic acid of F is converted into an amide (SEQ ID NO: 2). In one embodiment gastrin-17 has GenPept accession no. CAA25007.

The terms "mini gastrin" and "gastrin-14" are used interchangeably herein. In one embodiment the term "gastrin-14" is intended to mean human gastrin-14 which is defined by the amino acid sequence WLEEEEEAYG WMDF, wherein the C-terminal carboxylic acid of F is converted into an amide (SEQ ID NO: 3). In one embodiment gastrin-14 has SEQDB accession no. 0503136A.

In one embodiment gastrin binds to the gastrin receptor, CCK-2.

In one embodiment the gastrin derivative comprises the C-terminal amide of said gastrin.

The term "analogue" as used herein referring to a peptide is intended to mean a modified peptide wherein one or more amino acid residues of the peptide have been substituted by other amino acid residues and/or wherein one or more amino acid residues have been deleted from the peptide and/or wherein one or more amino acid residues have been added to the peptide and/or wherein one or more amino acid residues of the peptide have been modified. A simple nomenclature is used to describe the compounds according to the invention, for example, [Leu15]gastrin-17(4-17) designates an analogue of gastrin-17, wherein the naturally occurring methionine in position 15 has been substituted with leucine and the naturally occurring QGP in position 1-3 has been deleted. The peptide may be derived from vertebrates, such as human, mouse, sheep, goat, cow, or horse.

The term "fragment" as used herein referring to a gastrin is intended to mean that one or more consecutive amino acid residues have been deleted from the N-terminal or C-terminal end of said gastrin.

In one embodiment the invention relates to a derivative of gastrin-17 or a derivative of N-terminally truncated gastrin-17. In one embodiment the derivative may be attached to the N-terminal alpha-amino group of the gastrin.

The expressions a "position corresponds to" or "position corresponding to" may be used to characterise the site of modification in a modified gastrin sequence by reference to gastrin-17 (SEQ ID NO: 2). Corresponding positions are easily deduced, e.g. by simple handwriting and eyeballing; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12 and the penalties for additional residues in a gap at −2.

In one embodiment the gastrin derivative comprises deletion of the amino acids selected from the group consisting of position 1-13, 1-9,1-8, 1-7,1-6, 1-5,1-4, 1-3, 1-2 and 1, wherein said positions correspond to gastrin-17. In one embodiment the gastrin derivative comprises a deletion of the amino acids in position 1-13 in gastrin-17, wherein said positions correspond to gastrin-17. In one embodiment the gastrin derivative comprises a deletion of the amino acids in position 1-9, wherein said positions correspond to gastrin-17. In one embodiment the gastrin derivative comprises a deletion of the amino acids in positions 1-7, wherein said positions correspond to gastrin-17. In one embodiment the gastrin derivative comprises a deletion of the amino acids in position 1-5, wherein said positions correspond to gastrin-17.

In one embodiment the gastrin derivative comprises a substitution into lysine in a position selected from position 1-13, wherein said positions correspond to gastrin-17. In one embodiment the gastrin derivative comprises a substitution into lysine in a position selected from position 2-8, wherein said positions correspond to gastrin-17. In one embodiment the gastrin derivative comprises a substitution into lysine in position 2 or position 3, wherein said positions correspond to gastrin-17.

In one embodiment the gastrin comprises a substitution of methionine into leucine, such as substitution into Leu15, wherein said position corresponds to gastrin-17.

In one embodiment the gastrin derivatives described herein are stabilized against oxidation by leucine substitution in the position corresponding to position 15 in gastrin-17. In one embodiment gastrin derivatives having said Leu15 substitution have increased chemical stability.

In one embodiment the gastrin derivatives described herein comprise a sulphated tyrosine in the position corresponding to position 12 in gastrin-17.

In one embodiment the invention comprises peptides with at least 70%, 80%, 90%, 95% or 98% sequence identity to a gastrin of the invention over the entire length of said gastrin. As an example of a method for determination of sequence identity between two analogues the two peptides [Leu15] gastrin-17 and gastrin-17 are aligned. The sequence identity of the Leu15 analogue relative to gastrin-17 is given by the number of aligned identical residues minus the number of different residues divided by the total number of residues in gastrin-17. Accordingly, in said example the sequence identity is (17-1)/17.

In one embodiment one or more of the amino acids in the gastrin compound are the L-stereoisomer of said amino acid. In one embodiment one or more of the amino acids in the gastrin compound are the D-stereoisomer of said amino acid.

Derivatisation Groups

In one embodiment the gastrin derivative comprises a derivatisation group attached to an amino acid residue, e.g., the N-terminal amino group and/or a lysine side chain.

In one embodiment the derivatisation group comprises a $C_{12-22}$ acyl group. In one embodiment the derivatisation group comprises a $C_{14-20}$ acyl group, such as a $C_{16-18}$ acyl group In one embodiment the derivatisation group comprises one or more moieties selected from the group consisting of fatty acid, fatty diacid, tetrazole and linker.

In one embodiment the derivatisation group is A-B-C-D- or A-C-D- or A-B-C- or A-C- wherein A- is

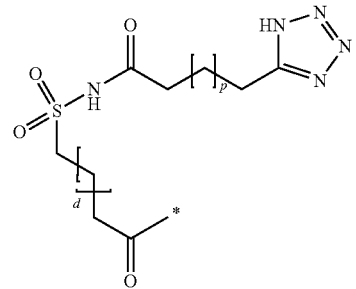

wherein p is selected from the group consisting of 10, 11, 12, 13 and 14, and d is selected from the group consisting of 0, 1, 2, 3, 4 and 5, and -B- is selected from the group consisting of

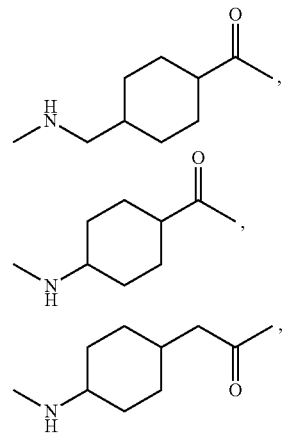

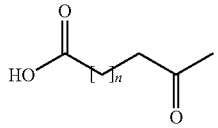

wherein x is selected from the group consisting of 0, 1, 2, 3 and 4, and y is selected from the group consisting of 1, 2, 3, 4, 5, 6, 7, 8, 9, 10, 11 and 12, or A- is

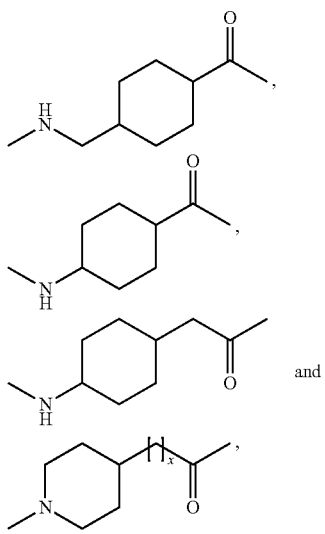

wherein n is selected from the group consisting of 12, 13, 14, 15, 16 17, 18 and 19, and B is selected from the group consisting of wherein x is selected from the group consisting of 0, 1, 2, 3 and 4, and -C- is selected from the group consisting of

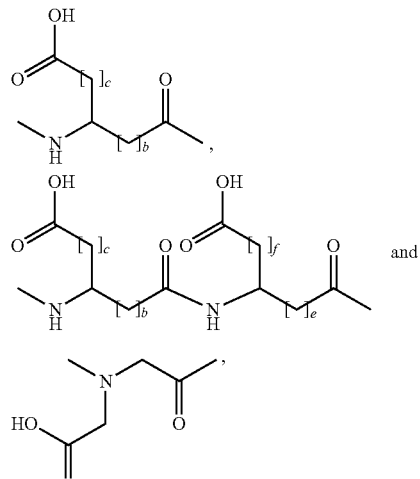

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker, is provided.

In one embodiment the derivatisation group is {2-(2-{2-[2-(2-{2-[4-Carboxy-4-(17-carboxyheptadecanoylamino) butyrylamino]ethoxy}-ethoxy)acetylamino]-ethoxy}ethoxy)acetyl}. In one embodiment {2-(2-{2-[2-(2-{2-[4-Carboxy-4-(17-carboxyheptadecanoylamino) butyrylamino]ethoxy}-ethoxy)acetylamino]-ethoxy}ethoxy)acetyl} is

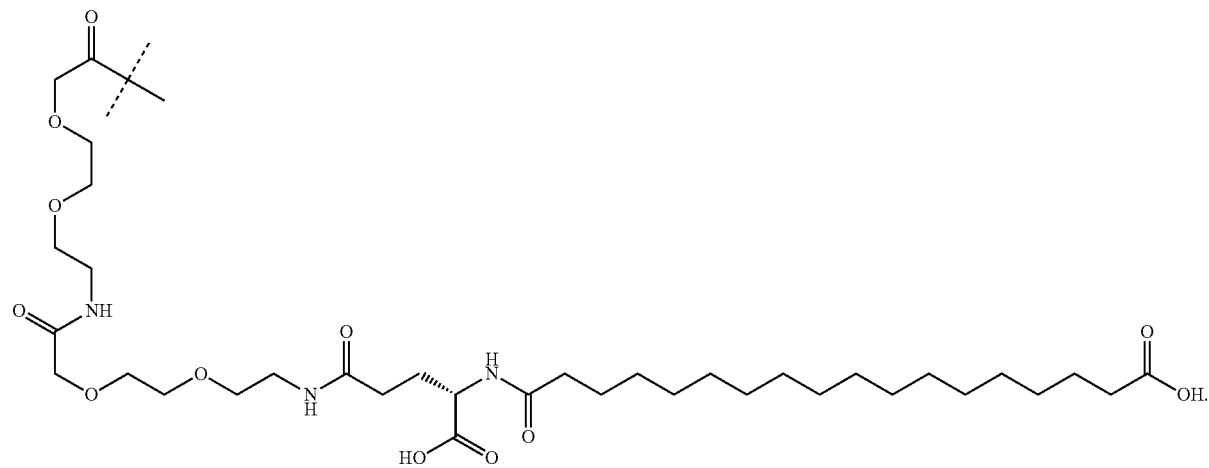

In one embodiment the derivatisation group is selected from the group consisting of 2-[2-[2-[[2-[2-[2-[[4-carboxy-4-(15-carboxypentadecanoylamino)butanoyl]amino]ethoxy]ethoxy]acetyl]amino]ethoxy]ethoxy]acetyl2-[2-[2-[[2-[2-[2-[[4-carboxy-4-(17-carboxyhepta-decanoylamino)butanoyl]amino]ethoxy]ethoxy]acetyl]amino]ethoxy]ethoxy]acetyl-; 2-[2-[2-[[2-[2-[[4-carboxy-4-(19-carboxynonadecanoylamino)butanoyl]amino]ethoxy]-ethoxy]acetyl]amino]ethoxy]ethoxy]acetyl-; 4-carboxy-4-(15-carboxypentadecanoylamino)-butanoyl-; 4-carboxy-4-(17-carboxyheptadecanoylamino)butanoyl-; 4-carboxy-4-(19-carboxynona-decanoylamino)butanoyl-; 17-carboxyheptadecanoyl-; 15-carboxypentadecanoyl-; 19-carboxynonadecanoyl-; 3[17-carboxyheptadecanoyl(carboxymethyl)amino]propanoyl-; 3-[15-carboxypentadecanoyl(carboxymethyl)amino]propanoyl-; 3419-carboxynona-decanoyl(carboxymethyl)amino]propanoyl-; 2-[2-[2-(17-carboxyheptadecanoylamino)ethoxy]ethoxy]acetyl-; 2-[2-[2-(15-carboxypentadecanoylamino)ethoxy]ethoxy]acetyl-; 2-[2-[2-(19-carboxynonadecanoylamino)ethoxy]ethoxy]acetyl-; (2-{2-[16-(Tetrazol-5-yl)hexadecanoyl-amino]-ethoxy}ethoxy)acetyl-; and 2-[2-(2-{2-[2-(2-{4-Carboxy-4]-10-(4-carboxyphenoxy) decanoylamino]-butyrylamino}ethoxy)ethoxy]-acetylamino}ethoxy)ethoxy]acetyl-.

In one embodiment the derivatisation group is selected from the group consisting of

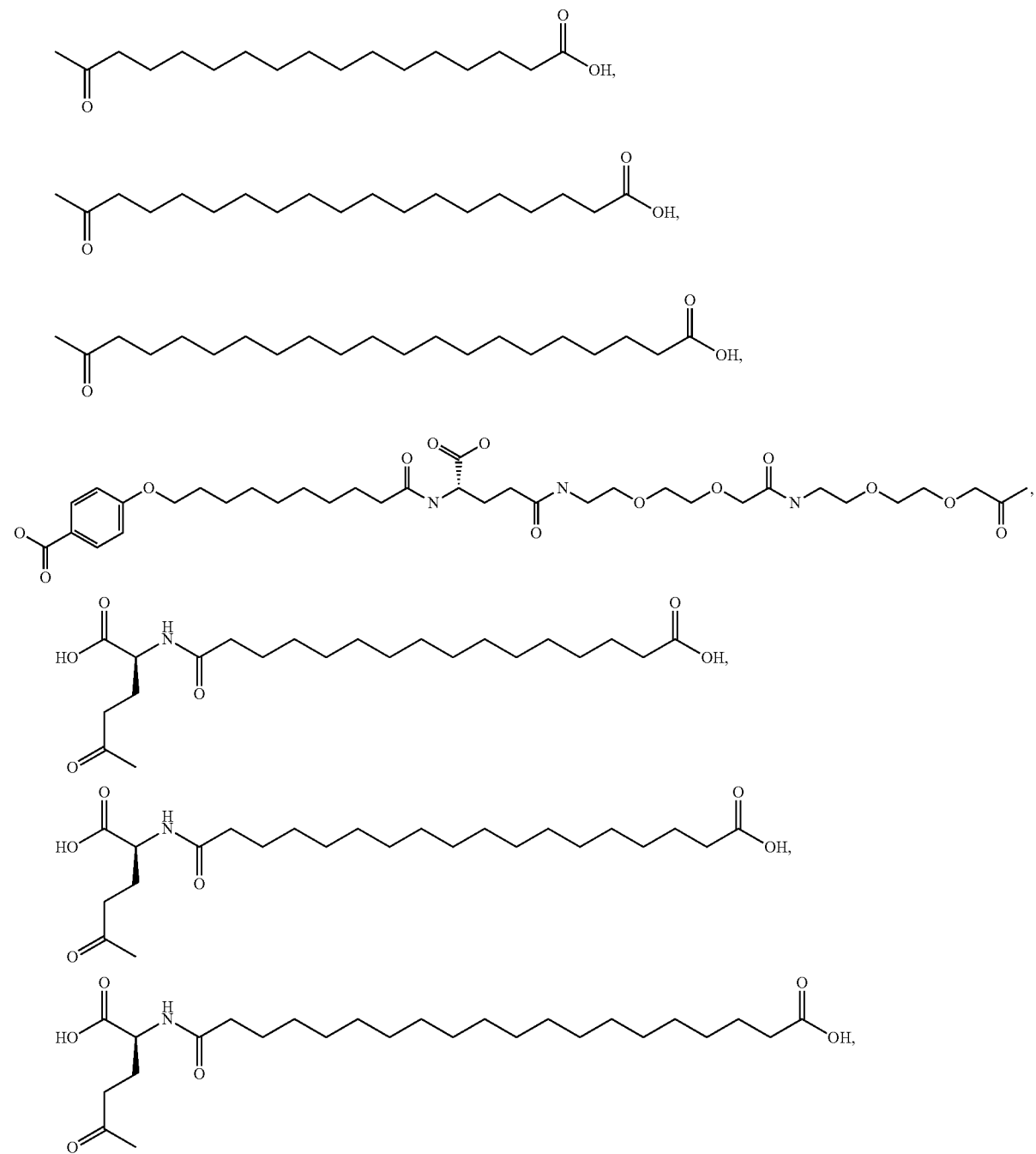

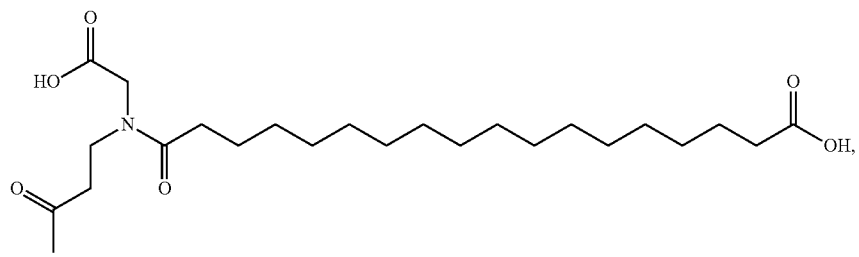
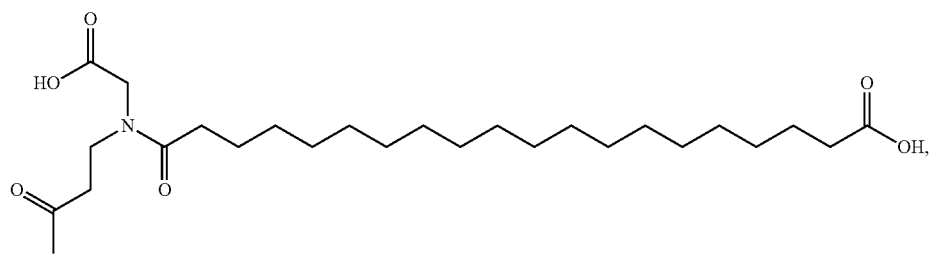
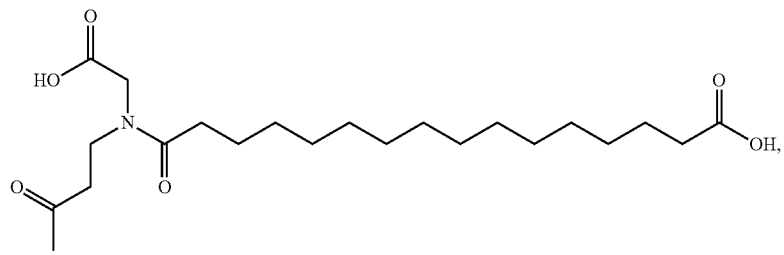
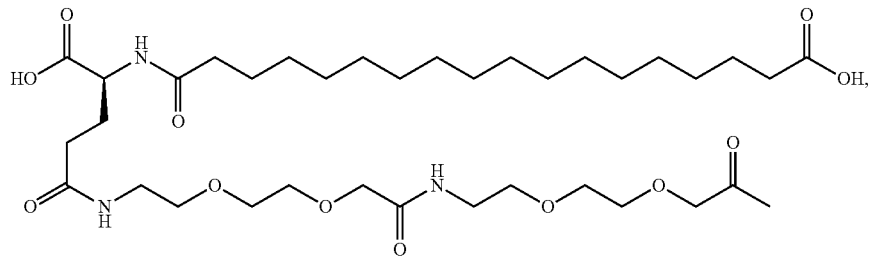
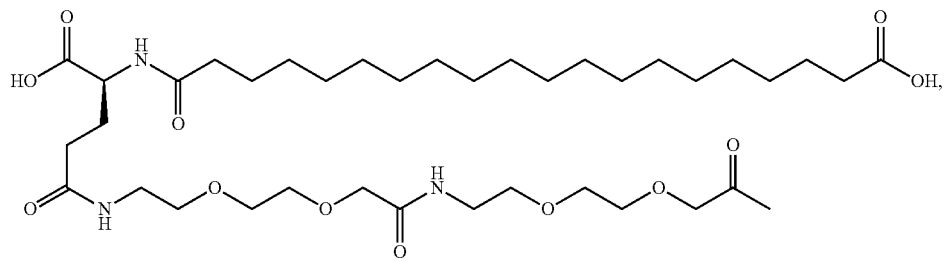
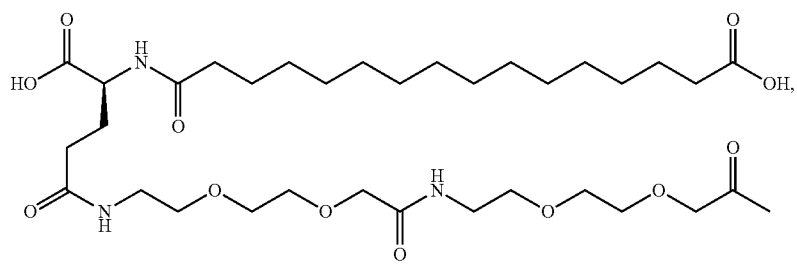

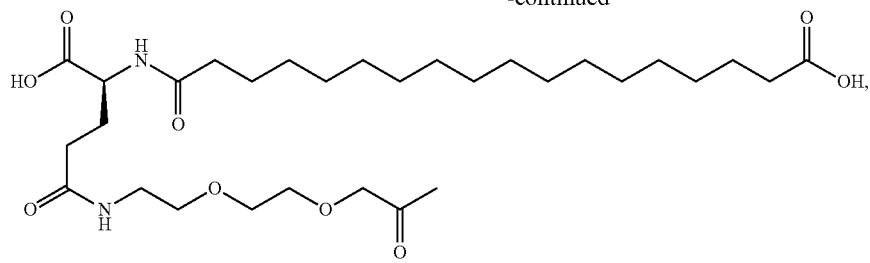
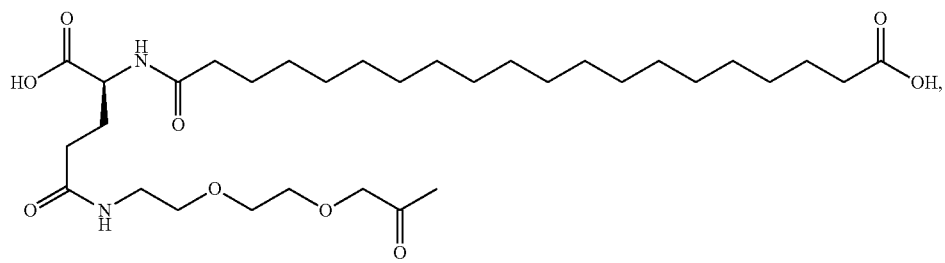
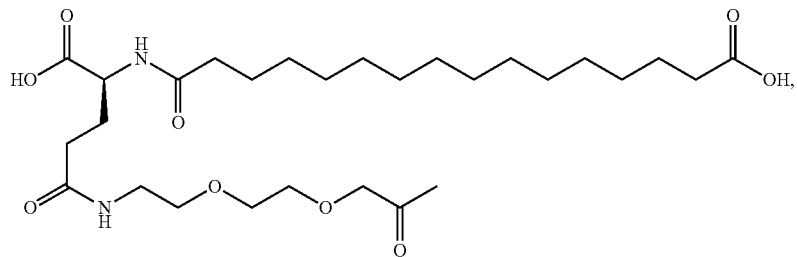
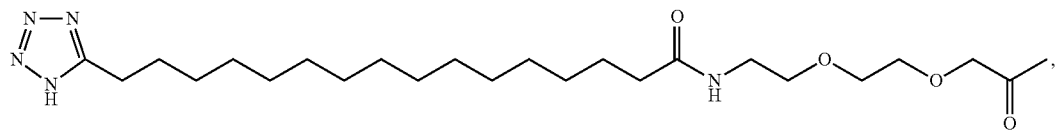
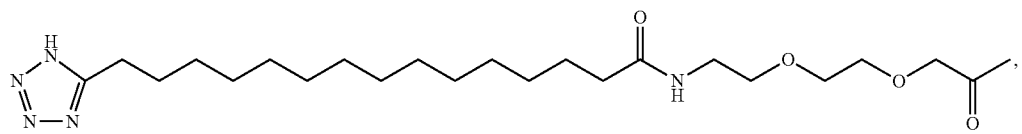
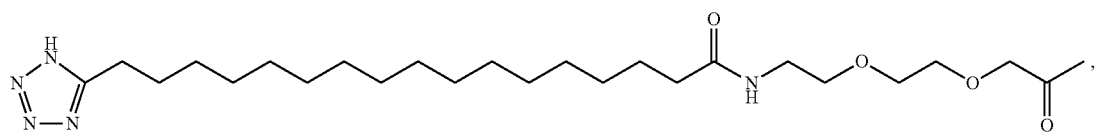
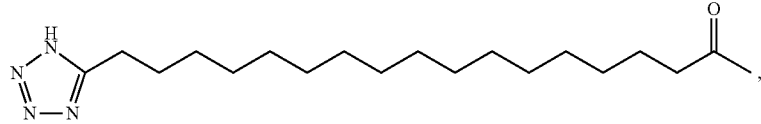
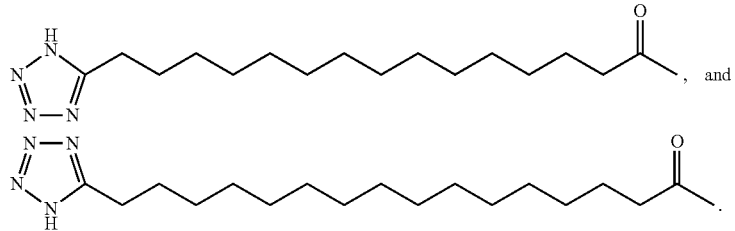

Gastrin Derivatives

In one embodiment the term "derivative" and "derivatisation group" are used interchangeably herein and as used herein in relation to a peptide means a chemically modified peptide, wherein at least one substituent is not present in the unmodified peptide, i.e. a peptide which has been covalently modified. In one embodiment said modifications are selected from the group consisting of amides, carbohydrates, alkyl groups, acyl groups and esters. In one embodiment said modifications include pegylation groups.

In one embodiment the gastrin derivative comprises a derivatisation group on the N-terminal alpha-amino group.

In one embodiment the gastrin derivative comprises a derivatisation group attached to the side chain of a lysine residue, such as to the epsilon amino group of a lysine residue.

In one embodiment the derivatisation group is attached to a position selected from the group consisting of the N-terminal amino group, position 2, 3, 4, 5, 6, 7, 8, 9, 10 or 11. In one embodiment the derivatisation group is attached to a position selected from the group consisting of the N-terminal amino group, position 2, 3, 4, 5, 6, 7 or 8. In one embodiment the derivatisation group is attached to position 2 or position 3, wherein the positions correspond to gastrin-17. In one embodiment the position referred to herein corresponds to gastrin-17.

In one embodiment the gastrin derivative comprises positions 11 through 17 of gastrin-17.

In one embodiment the gastrin derivative comprises gastrin and a derivatisation group on the N-terminal alpha-amino group of said gastrin, wherein said gastrin is selected from the group consisting of
  Gastrin-17(1-17) (A),
  Gastrin-17(2-17) (B),
  Gastrin-17(3-17) (C),
  Gastrin-17(4-17) (D),
  Gastrin-17(5-17) (E),
  Gastrin-17(6-17) (F),
  Gastrin-17(7-17) (G),
  Gastrin-17(8-17) (H),
  Gastrin-17(9-17) (I),
  Gastrin-17(10-17) (J),
  Gastrin-17(11-17) (K),
  Gastrin-17(12-17) (L) and
  Gastrin-17(13-17) (M).

In one embodiment the invention relates to a derivative of gastrin-17 comprising a derivatisation group on an amino acid residue in any one of positions 1-13 relative to gastrin-17.

In one embodiment the gastrin derivative is selected from the group consisting of
  [Lys1]Gastrin-17(1-17) (N),
  [Lys2]Gastrin-17(1-17) (O),
  [Lys3]Gastrin-17(1-17) (P),
  [Lys4]Gastrin-17(1-17) (O),
  [Lys5]Gastrin-17(1-17) (R),
  [Lys6]Gastrin-17(1-17) (S),
  [Lys7]Gastrin-17(1-17) (T),
  [Lys8]Gastrin-17(1-17) (U),
  [Lys9]Gastrin-17(1-17) (V),
  [Lys10]Gastrin-17(1-17) (X),
  [Lys11]Gastrin-17(1-17) (Y),
  [Lys12]Gastrin-17(1-17) (Z) and
  [Lys13]Gastrin-17(1-17) (AA),
wherein said lysine residue comprises a derivatisation group.

In one embodiment the gastrin derivative is N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}gastrin-17.

In one embodiment the gastrin derivative is N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}[Leu 15] gastrin-17.

In one embodiment the gastrin derivative is N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}[Leu 15] gastrin-17(4-17).

In one embodiment the gastrin derivative is N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}[Leu 15] gastrin-17(7-17).

Gastrin analogues may be prepared synthetically by either solid-phase or solution peptide synthesis methods as described herein. The N-terminal amino group or epsilon-amino group of an internal lysine residue may be chemically acylated as described herein and the final product may be purified by reversed-phase or other chromatographic methods, as described herein.

Effects of Gastrin Derivatives

Receptor interaction with gastrin analogues may be determined in an in vitro assay measuring gastrin receptor (CCK2R) mediated calcium release in a cell line which overexpresses CCK-2R, e.g., according to Assay (I).

In one embodiment the gastrin derivatives have CCK2R binding of no less than 1% of human gastrin-17 as determined by Assay (I) and/or the gastrin derivatives have a longer half life than human gastrin-17 as determined by Assay (II). In one embodiment said longer half life provides the gastrin derivative with sufficient plasma residence time to result in less frequent dosing regime than that of human gastrin-17.

Plasma half life may be determined in rat and/or mini pigs, e.g., according to Assay (II). In one embodiment the half-life of the gastrin derivative is at least 100, such as at least 500, times the half-life of gastrin-17, wherein said half-life is determined by Assay (II).

In one embodiment the gastrin derivative may be used in medicine. In one embodiment the gastrin derivative may be used for stimulation of beta cell proliferation, treatment of or reduction of symptoms associated with type 1 diabetes or type 2 diabetes, or treatment of diabetes, hypertension, chronic heart failure, fluid retentive states, obesity or metabolic syndrome. In one embodiment the invention relates to the use of the gastrin derivative for the preparation of a medicament for the stimulation of beta cell proliferation, treatment of or reduction of symptoms associated with type 1 diabetes or type 2 diabetes, or treatment of diabetes, hypertension, chronic heart failure, fluid retentive states, obesity or metabolic syndrome. In one embodiment the invention relates to a method for stimulation of beta cell proliferation, treatment of or reduction of symptoms associated with type 1 diabetes or type 2 diabetes, or treatment of diabetes, hypertension, chronic heart failure, fluid retentive states, obesity or metabolic syndrome by administration of a gastrin derivative according to any one of the preceding embodiments. In one embodiment the gastrin derivative is used for the treatment of cardiovascular disease. In one embodiment the gastrin derivative provides a reduction in weight gain. In one embodiment the gastrin derivative is administered once daily or less frequently, such as once weekly or less frequently.

Pharmaceutical Compositions

In one embodiment the invention relates to a composition comprising a gastrin derivative as defined herein and one or more pharmaceutical excipients. In one embodiment the dosing regime for the gastrin derivative is once daily or once weekly.

In one embodiment the composition comprising a gastrin derivative further comprises a protein pump inhibitor.

Embodiments of the Invention

The following are additional particular embodiments of the invention:

1. A gastrin derivative comprising gastrin or an analogue or fragment thereof and a derivatisation group.
2. The gastrin derivative according to any one of the preceding embodiments, wherein said derivatisation group is attached to a position selected from the group consisting of the N-terminal amino group, position 2, 3, 4, 5, 6, 7, 8, 9, 10 or 11.
3. The gastrin derivative according to any one of the preceding embodiments, wherein said derivatisation group is attached to a position selected from the group consisting of the N-terminal amino group, position 2, 3, 4, 5, 6, 7 or 8.
4. The gastrin derivative according to any one of the preceding embodiments, wherein said derivatisation group is attached to position 2 or position 3, wherein the positions correspond to gastrin-17.
5. The gastrin derivative according to any one of the preceding embodiments, wherein said derivatisation group comprises a $C_{12-22}$ acyl group.
6. The gastrin derivative according to any one of the preceding embodiments, wherein said derivatisation group comprises one or more moieties selected from the group consisting of fatty acid, fatty diacid, tetrazole and linker.
7. The gastrin derivative according to any one of the preceding embodiments, wherein said derivatisation group is A-B-C-D- or A-C-D- or A-B-C- or A-C -wherein A- is

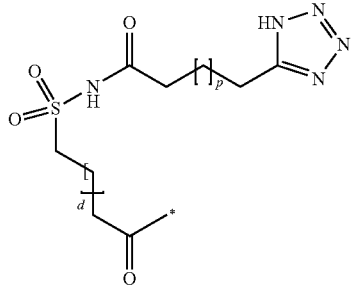

wherein p is selected from the group consisting of 10, 11, 12, 13 and 14, and d is selected from the group consisting of 0, 1, 2, 3, 4 and 5, and -B- is selected from the group consisting of

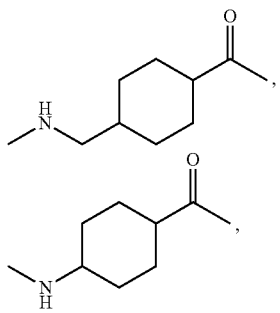

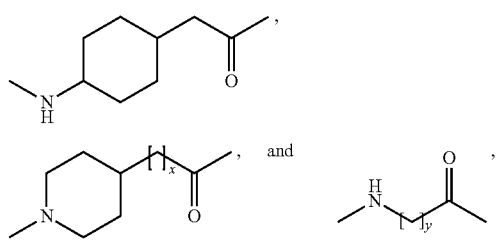

wherein x is selected from the group consisting of 0, 1, 2, 3 and 4, and y is selected from the group consisting of 1, 2, 3, 4, 5, 6, 7, 8, 9, 10, 11 and 12, or A- is

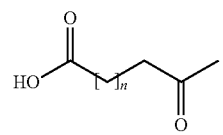

wherein n is selected from the group consisting of 12, 13, 14, 15, 16 17, 18 and 19, and B is selected from the group consisting of

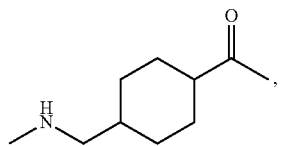

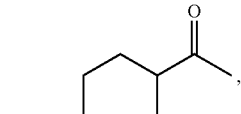

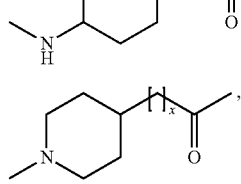

wherein x is selected from the group consisting of 0, 1, 2, 3 and 4, and

-C- is selected from the group consisting of

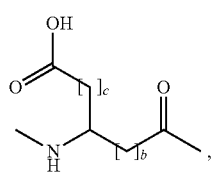

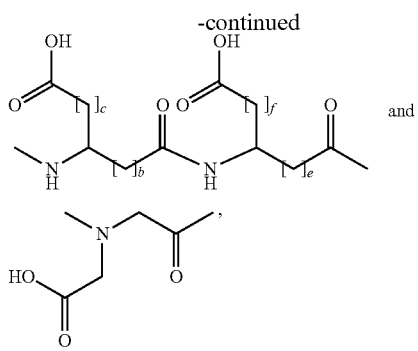

and wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker, is provided.

8. The gastrin derivative according to any one of the preceding embodiments, wherein said derivatisation group is selected from the group consisting of 2-[2-[2-[[2-[2-[2-[[4-carboxy-4-(15-carboxypentadecanoylamino)butanoyl]amino]-ethoxy]ethoxy]acetyl]amino]ethoxy]ethoxy]acetyl2-[2-[2-[[2-[2-[2-[[4-carboxy-4-(17-carboxyheptadecanoylamino)butanoyl]amino]ethoxy]ethoxy]acetyl]amino]ethoxy]ethoxy]acetyl-; 2-[2-[2-[[2-[2-[2-[[4-carboxy-4-(19-carboxynonadecanoylamino)butanoyl]amino]ethoxy]ethoxy]acetyl]amino]ethoxy]ethoxy]acetyl-; 4-carboxy-4-(15-carboxypentadecanoylamino)-butanoyl-; 4-carboxy-4-(17-carboxyheptadecanoylamino)butanoyl-; 4-carboxy-4-(19-carboxynonadecanoylamino)butanoyl-; 17-carboxyheptadecanoyl-; 15-carboxypentadecanoyl-; 19-carboxynonadecanoyl-; 3-[17-carboxyheptadecanoyl(carboxymethyl)amino]propanoyl-; 3-[15-carboxypentadecanoyl(carboxymethyl)amino]propanoyl-; 3-[19-carboxynonadecanoyl(carboxymethyl)amino]propanoyl-; 2-[2-[2-(17-carboxyheptadecanoylamino)ethoxy]ethoxy]acetyl-; 2-[2-[2-(15-carboxypentadecanoylamino)ethoxy]ethoxy]acetyl-; 2-[2-[2-(19-carboxynonadecanoylamino)ethoxy]ethoxy]acetyl-; (2-{2-[16-(Tetrazol-5-yl)hexadecanoyl-amino]-ethoxy}ethoxy)acetyl-; and 2-[2-(2-{2-[2-(2-{4-Carboxy-4-[10-(4-carboxyphenoxy)decanoylamino]-butyrylamino}ethoxy)ethoxy]-acetylamino}ethoxy)ethoxy]acetyl-.

9. The gastrin derivative according to any one of the preceding embodiments, wherein said derivatisation group is {2-(2-{2-[2-(2-{2-[4-Carboxy-4-(17-carboxyheptadecanoylamino)butyrylamino]ethoxy}-ethoxy)acetylamino]-ethoxy}ethoxy)acetyl}.

10. The gastrin derivative according to any one of the preceding embodiments, wherein said gastrin is selected from the group consisting of gastrin-34, gastrin-17 and gastrin-14.

11. The gastrin derivative according to any one of the preceding embodiments, wherein said gastrin comprises a substitution of methionine into leucine, such as substitution into Leu15, wherein said position corresponds to gastrin-17.

12. The gastrin derivative according to any one of the preceding embodiments, wherein said gastrin derivative comprises deletion of the amino acids selected from the group consisting of position 1-13, 1-9,1-8, 1-7,1-6, 1-5,1-4, 1-3, 1-2 and 1, wherein said positions correspond to gastrin-17.

13. The gastrin derivative according to any one of the preceding embodiments, wherein said gastrin derivative comprises a deletion of the amino acids in position 1-13 in gastrin-17, wherein said positions correspond to gastrin-17.

14. The gastrin derivative according to any one of the preceding embodiments, wherein said gastrin derivative comprises a deletion of the amino acids in position 1-9, wherein said positions correspond to gastrin-17.

15. The gastrin derivative according to any one of the preceding embodiments, wherein said gastrin derivative comprises a deletion of the amino acids in positions 1-7, wherein said positions correspond to gastrin-17.

16. The gastrin derivative according to any one of the preceding embodiments, wherein said gastrin derivative comprises a deletion of the amino acids in position 1-5, wherein said positions correspond to gastrin-17.

17. The gastrin derivative according to any one of the preceding embodiments, wherein said gastrin derivative comprises a substitution into lysine in a position selected from position 1-13, wherein said positions correspond to gastrin-17.

18. The gastrin derivative according to any one of the preceding embodiments, wherein said gastrin derivative comprises a substitution into lysine in a position selected from position 2-8, wherein said positions correspond to gastrin-17.

19. The gastrin derivative according to any one of the preceding embodiments, wherein said gastrin derivative comprises a substitution into lysine in position 2 or position 3, wherein said positions correspond to gastrin-17.

20. The gastrin derivative according to any one of the preceding embodiments, wherein said gastrin derivative is selected from the group consisting of
Gastrin-17(1-17) (A),
Gastrin-17(2-17) (B),
Gastrin-17(3-17) (C),
Gastrin-17(4-17) (D),
Gastrin-17(5-17) (E),
Gastrin-17(6-17) (F),
Gastrin-17(7-17) (G),
Gastrin-17(8-17) (H),
Gastrin-17(9-17) (I),
Gastrin-17(10-17) (J),
Gastrin-17(11-17) (K),
Gastrin-17(12-17) (L) and
Gastrin-17(13-17) (M), and wherein said gastrin derivative comprises a derivatisation group attached to the N-terminal amino group.

21. The gastrin derivative according to any one of the preceding embodiments, wherein said gastrin derivative is selected from the group consisting of
[Lys1]Gastrin-17(1-17) (N),
[Lys2]Gastrin-17(1-17) (O),
[Lys3]Gastrin-17(1-17) (P),
[Lys4]Gastrin-17(1-17) (Q),
[Lys5]Gastrin-17(1-17) (R),
[Lys6]Gastrin-17(1-17) (S),
[Lys7]Gastrin-17(1-17) (T),
[Lys8]Gastrin-17(1-17) (U),
[Lys9]Gastrin-17(1-17) (V),
[Lys10]Gastrin-17(1-17) (X),
[Lys11]Gastrin-17(1-17) (Y),
[Lys12]Gastrin-17(1-17) (Z) and
[Lys13]Gastrin-17(1-17) (AA), and wherein said lysine residue comprises a derivatisation group.

22. The gastrin derivative according to any one of the preceding embodiments, wherein said gastrin derivative is N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}gastrin-17 or N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}[Leu15] gastrin-17 (1-17).
23. The gastrin derivative according to any one of the preceding embodiments, wherein the half-life of said gastrin derivative is at least 100, such as at least 500, times the half-life of gastrin-17, wherein said half-life is determined by Assay (II).
24. The gastrin derivative according to any one of the preceding embodiments for use in medicine.
25. The gastrin derivative according to any one of the preceding embodiments for the stimulation of beta cell proliferation, treatment of or reduction of symptoms associated with type 1 diabetes or type 2 diabetes, or treatment of diabetes, hypertension, chronic heart failure, fluid retentive states, obesity or metabolic syndrome.
26. Use of the gastrin derivative according to any one of the preceding embodiments for the preparation of a medicament for the stimulation of beta cell proliferation, treatment of or reduction of symptoms associated with type 1 diabetes or type 2 diabetes, or treatment of diabetes, hypertension, chronic heart failure, fluid retentive states, obesity or metabolic syndrome.
27. A method for stimulation of beta cell proliferation, treatment of or reduction of symptoms associated with type 1 diabetes or type 2 diabetes, or treatment of diabetes, hypertension, chronic heart failure, fluid retentive states, obesity or metabolic syndrome by administration of a gastrin derivative according to any one of the preceding embodiments.
28. A gastrin derivative according to any one of embodiment 1-24, wherein said gastrin derivative is administered once daily or less frequently, such as once weekly or less frequently.
29. A method according to embodiment 26, wherein said gastrin derivative is administered once daily or less frequently, such as once weekly or less frequently.
30. A composition comprising a gastrin derivative according to any one of embodiment 1-24 and more or more pharmaceutical excipients.

EXAMPLES

General Method for Peptide Synthesis
The Fmoc-protected amino acid derivatives used were:
Fmoc-Ala-OH
Fmoc-Arg(Pbf)-OH
Fmoc-Asn(Trt)-OH
Fmoc-Asp(OtBu)-OH
Fmoc-Cys(Trt)-OH
Fmoc-Gln(Trt)-OH
Fmoc-Glu(OtBu)-OH
Fmoc-Gly-OH
Fmoc-His(Trt)-OH
Fmoc-Ile-OH
Fmoc-Leu-OH
Fmoc-Lys(Boc)-OH
Fmoc-Met-OH
Fmoc-Phe-OH
Fmoc-Pro-OH
Fmoc-Ser(tBu)-OH
Fmoc-Thr(tBu)-OH
Fmoc-Trp(Boc)-OH
Fmoc-Tyr(tBu)-OH
Fmoc-Val-OH supplied from e.g. Anaspec, Bachem, Iris Biotech, or Novabiochem. When an acylation was present on a lysine side chain the epsilon amino group of lysine to be acylated was protected with Mtt (e.g. Fmoc-Lys(Mtt)-OH) and the N-terminal alpha amino group was protected with Boc (e.g. Boc-Gln(Trt)-OH). Tyrosine sulfate residues were introduced using Fmoc-Tyr(SO3.NnBu4)—OH available from Novabiochem. The synthesis of the peptides may in some cases be improved by the use of dipeptides, e.g., pseudoprolines from Novabiochem, Fmoc-Ser(tBu)-ΨSer(Me,Me)-OH, see e.g. catalogue from Novabiochem 2002/2003 or newer version, or W. R. Sampson (1999), J. Pep. Sci. 5, 403. Where nothing else is specified the natural L-form of the amino acids were used.

Synthesis of Cellulose Bound Peptides (SCBP)

The peptides were synthesized in double (two copies) on standard amino-modified acid stable cellulose membrane with PEG-Spacer from AIMS Scientific Products GmbH (Germany) in 96-well format using a fully automated Multi-Pep robot from Intavis Bioanalytical Instruments (Germany) equipped with the AutoSpot module. Couplings were performed in triple using HOAt/DIPCDI/collidine preactivation (0.4 µl 1 M DIC in NMP, 0.2 µl 1 M collidine in NMP, 0.3 M Fmoc amino acid in 0.3 M HOAt in NMP per SPOT for 30 min). Fmoc deprotection was performed by treating each membrane with 20% piperidine in NMP (2×6 ml) for 10 min. Membrane washing was with NMP (6×6 ml) and EtOH (6×6 ml) via the robot manifold followed by drying. The membrane was first derivatized with Fmoc-Gly-OH/Boc-Gly-OH (1:1) followed by capping with NMP/AcO$_2$/DIPEA (94:5:1) (SPOT definition and membrane loading adjustment) and washing. After Fmoc removal, coupling of Fmoc-Photo-Linker (RL-1026, available from Iris Biotech GmbH), and washing. The peptides were synthesized using the repetitive cycle of deprotection, coupling and washing. When the peptide backbone sequence was completed the membrane was treated with HFIP/DCM (75:25, 3×20 ml) for 10 min followed by positive bromophenolblue test. The derivatisation group was then introduced using the repetitive cycle of deprotection, coupling and washing. The following building blocks were used Fmoc-Oeg-OH, Fmoc-Glu-OtBu, and C18diacid mono tert-butyl ester.

Syntheisis of Resin Bound Peptide (SRBP)

The protected peptidyl resin was synthesized according to the Fmoc strategy on a Prelude Solid Phase Peptide Synthesizer from Protein Technologies in 0.25 mmol scale. The resin used for the synthesis of the peptide amides was TentaGel S RAM (0.25 mmol/g, 1 g) from Rapp Poymere GmbH. The resin was swelled in DCM (5 ml, 5 min) and drained. The following representative procedure was used: 20% piperidine (2×7 ml) was added and the resin was agitated for 5 min. The resin was washed with DCM (6 ml), NMP (2×7 ml), DCM (8 ml), and NMP (2×7 ml). 0.3 M Fmoc-amino acid in 0.3 M HOAt in NMP (5 ml), 3 M DIC in NMP (500 µl), and 3 M collidine in NMP (650 µl) were added and the resin was agitated for 45 min. The resin was drained and washed with DCM (6 ml), NMP (2×7 ml), DCM (8 ml), and NMP (2×7 ml). This procedure was repeated for each amino acid in the peptide backbone sequence. Some amino acids, including but not limited to Fmoc-Arg(Pbf)-OH, Fmoc-Aib-OH, Fmoc-His(Trt)-OH, Fmoc-Glu(OtBu)-OH were "double coupled", meaning that after the first coupling, the resin is drained and more reagents are added (amino acid, HOAt, DIC, and collidine), and the mixture allowed to react again. When the peptide backbone sequence was completed the derivatisation group was introduced using the above stated coupling procedure with the modification that the amino acids and fatty acid derivatives including Fmoc-Oeg-OH, Fmoc-Glu-OtBu, and octadecanedioic acid mono-tert-butyl ester were coupled for 6 hrs and after coupling the resin was capped for 5 min with 1 M $Ac_2O$ in NMP (5 ml) and collidine (500 µl). In case of acylation on a lysine epsilon group, the Mtt protection group was removed prior to coupling of the albumin binding moiety by washing the resin with DCM (6×5 ml) and treating it with HFIP/DCM (75:25) (4×5 ml) for 10 min followed by washing with DCM (3×6 ml), NMP (3×6 ml).

Cleavage of Resin Bound Peptide (CRBP)

After synthesis the resin was washed with DCM and dried, and the peptide was cleaved from the resin by a 2 hour treatment with TFA/TIPS/water (92.5/5.0/2.5) followed by precipitation with diethylether. The peptide was redissolved in 0.25M $NH_4HCO_3$(aq) and purified by standard RP-HPLC on a C18 column using a gradient of 0.25 M $NH_4HCO_3$(aq) and 10-40% acetonitrile. The identity of the peptide was confirmed by MALDI-MS or LC-MS and the fractions lyophilized yielding the pure peptide ready for assays, Cleavage of Celloluse Bound Peptides (CCBP)

After synthesis the cellulose membrane was washed with DCM (5×20 ml), dried, and the side chain protection groups were removed by a 2 hour treatment with TFA/TIPS/water (92.5/5.0/2.5) followed by washings with DCM (5×20 ml), NMP (5×20 ml), and EtOH (5×20 ml). The dried membrane was placed on a transilluminator irradiating at 365 nm for 3 hrs. The SPOT were punched out and placed in a filtration 96-well miroplate. 40 µl DMSO was added to each SPOT and the plate was shaken for 30 min. The filtrate from each well was collected and 160 µl HBSS 1× with 20 mM Hepes, 0.1% ovalbumin, 0.005% Tween20 was added to each well yielding the crude peptides in solution ready for assays.

Ultra Performance Liquid Chromatography (UPLC) Method (Method 08_B4_1)

UPLC (method 08_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:

A: 99.95% $H_2O$, 0.05% TFA and
B: 99.95% $CH_3CN$, 0.05% TFA.

The following linear gradient was used: 95% A, 5% B to 95% A, 5% B over 16 minutes at a flow-rate of 0.40 ml/min.

Ultra Performance Liquid Chromatography (UPLC) Method (Method 04_A3_1)

UPLC (method 04_A3_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:

A: 90% $H_2O$, 10% $CH_3CN$, 0.25 M ammonium bicarbonate and
B: 70% $CH_3CN$, 30% $H_2O$.

The following linear gradient was used: 75% A, 25% B to 45% A, 55% B over 16 minutes at a flow-rate of 0.40 ml/min.

Ultra Performance Liquid Chromatography (UPLC) Method (Method 04_A6_1)

UPLC (method 04_A3_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:

A: 10 mM TRIS, 15 mM ammonium sulphate, 80% $H_2O$, 20%, pH 7.3;
B: 80% $CH_3CN$, 20% $H_2O$.

The following linear gradient was used: 95% A, 5% B to 10% A, 90% B over 16 minutes at a flow-rate of 0.35 ml/min.

Liquid Chromatography-Mass Spectrometry (LCMS) Method 4 (LCMS4)

LCMS4 was performed on a setup consisting of Waters Acquity UPLC system and LCT Premier XE mass spectrometer from Micromass. The UPLC pump was connected to two eluent reservoirs containing:

A: 0.1% Formic acid in water and
B: 0.1% Formic acid in acetonitrile.

The analysis was performed at room temperature by injecting an appropriate volume of the sample (preferably 2-10 µl) onto the column which was eluted with a gradient of A and B. The UPLC conditions, detector settings and mass spectrometer settings were:

Column: Waters Acquity UPLC BEH, C-18, 1.7 µm, 2.1 mm×50 mm;
Gradient: Linear 5%-95% acetonitrile during 4.0 min (alternatively 8.0 min) at 0.4 ml/min;
Detection: 214 nm (analogue output from TUV (Tunable UV detector));
MS ionisation mode: API-ES; and
Scan: 100-2000 amu (alternatively 500-2000 amu), step 0.1 amu.

Matrix-Assisted Laser Desorption and Ionization (MALDI) Method

Molecular weights were determined using matrix-assisted laser desorption and ionization time-of-flight mass spectroscopy, recorded on a Microflex or Autoflex (Bruker). A matrix of alpha-cyano-4-hydroxy cinnamic acid was used.

Example 1

Preparation Method: General Method for Peptide Synthesis (SRBP and CRBP), As Described Herein N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}[Gln1] gastrin-17 (A)
UPLC (method 08_B4_1): Rt 9.8 min
UPLC (method 04_A3_1): Rt 6.6 min
LCMS (LCMS4): m/z=944 $(M+3H)^{3+}$, 1416 $(M+2H)^{2+}$ Example 2

Preparation Method: General Method for Peptide Synthesis (SRBP and CRBP), As Described Herein N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}[Gln1,Leu15] gastrin-17
UPLC (method 08_B4_1): Rt 9.9 min
UPLC (method 04_A3_1): Rt 6.9 min
LCMS (LCMS4): m/z=939 $(M+3H)^{3+}$, 1408 $(M+2H)^{2+}$ Example 3

Preparation Method: General Method for Peptide Synthesis (SRBP and CRBP), as Described Herein N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}[Leu15] gastrin-17 (4-17)

UPLC (method 08_B4_1): Rt 10.3 min
UPLC (method 04_A3_1): Rt 7.6 min
LCMS (LCMS4): m/z=844 (M+3H)$^{3+}$, 1266 (M+2H)$^{2+}$ Example 4

Preparation Method: General Method for Peptide Synthesis (SRBP and CRBP), as Described Herein N-alpha-{2-(2-{2-[2-(2-{2-[4-Carboxy-4-(17-carboxy-heptadecanoylamino)butyrylamino]ethoxy}-ethoxy)acetylamino]-ethoxy}ethoxy)acetyl}[Leu15] gastrin-17 (7-17)
UPLC (method 08_B4_1): Rt 9.8 min
UPLC (method 04_A3_1): Rt 6.1 min
LCMS (LCMS4): m/z=1052 (M+2H)$^{2+}$ Example 5

Preparation Method General Method for Peptide Synthesis (SRBP and CRBP), as Described Herein N-Epsilon-3-}-[2-[2-[2-[16-(1H-tetrazol-5-1)hexadecanoylamino]ethoxy]ethoxy]acetyl]-[Lys3,Leu15] gastrin-17
UPLC (method 04_A6_1): Rt 5.5 min
LCMS (LCMS4): m/z=1282 (M+2H)$^{2+}$ Example 6

Preparation Method: General Method for Peptide Synthesis (SRBP and CRBP), as Described Herein N{Epsilon-8}-[2-[2-[2-[[2-[2-[2-[[(4S)-4-carboxy-4-(19-carboxynondecanoylamino)butanoyl]amino]ethoxy]ethoxy]acetyl]amino]ethoxy]ethoxy]acetyl-[Lys8,Leu15] gastrin-17
UPLC (method 04_A6_1): Rt 6.4 min
MALDI m/z=2823

Example 7

Preparation Method: General Method for Peptide Synthesis (SRBP and CRBP), as Described Herein N{Epsilon-14}-[2-[2-[2-[[(4S)-4-carboxy-4-(15-carboxypentadecanoylamino)butanoyl]amino]ethoxy]ethoxy]acetyl]-[Lys14,Leu15] gastrin-17
UPLC (method 04_A6_1): Rt 8.3 min
MALDI m/z=2533

Example 8

Preparation Method: General Method for Peptide Synthesis (SCBP and CCBP), as Described Herein The following gastrin compounds were been prepared:
[Leu15] Gastrin-17;
N-α-#-[Leu 15] Gastrin-17;
N-α-#-[Leu15] Gastrin-17 (2-17);
N-α-#-[Leu15] Gastrin-17 (3-17);
N-α-#-[Leu15] Gastrin-17 (4-17);
N-α-#-[Leu15] Gastrin-17 (5-17);
N-α-#-[Leu15] Gastrin-17 (6-17);
N-α-#-[Leu15] Gastrin-17 (7-17);
N-α-#-[Leu15] Gastrin-17 (8-17);
N-α-#-[Leu15] Gastrin-17 (9-17);
N-α-#-[Leu15] Gastrin-17 (10-17);
N-α-#-[Leu 15] Gastrin-17 (11-17);
N-α-#-[Leu15] Gastrin-17 (12-17);
N-α-#-[Leu15] Gastrin-17 (13-17);
N-α-#-[Leu15] Gastrin-17 (14-17);
N-α-#-[Leu15] Gastrin-17 (15-17);
N-α-#-[Leu15] Gastrin-17 (16-17);
[Lys2(N-ε-#),Leu15] Gastrin-17;
[Lys3(N-ε-#),Leu15] Gastrin-17;
[Lys4(N-ε-#),Leu15] Gastrin-17;
[Lys5(N-ε-#),Leu15] Gastrin-17;
[Lys6(N-ε-#),Leu15] Gastrin-17;
[Lys7(N-ε-#),Leu15] Gastrin-17;
[Lys8(N-ε-#),Leu15] Gastrin-17;
[Lys9(N-ε-#),Leu15] Gastrin-17;
[Lys10(N-ε-#),Leu15] Gastrin-17;
[Lys11(N-ε-#),Leu15] Gastrin-17;
[Lys12(N-ε-#),Leu15] Gastrin-17;
[Lys13(N-ε-#),Leu15] Gastrin-17;
[Lys14(N-ε-#),Leu15] Gastrin-17;
[Lys15(N-ε-#),Leu15] Gastrin-17; and
[Lys16(N-ε-#),Leu15] Gastrin-17,
wherein # is {2-(2-{2-[2-(2-{2-[4-Carboxy-4-(17-carboxy-heptadecanoylamino)butyrylamino]ethoxy}-ethoxy)acetylamino]-ethoxy}ethoxy)acetyl} and wherein gastrin-17 is as defined by SEQ ID NO: 2.

Pharmacological Methods

Assay (I): In Vitro Receptor Potency

In vitro receptor potency was measured using a CCK2 receptor mediated calcium mobilization assay. The CCK2 receptor (gastrin receptor) signals via the heterotrimeric G-protein, Gq, to activate phospholipase C(PLC). This leads to generation of inositol-1,4,5-trisphosphate (IP3) that releases calcium from intracellular stores. The primary rise in cytosolic calcium concentration is followed by activation of calcium dependent calcium channels in the plasma membrane allowing extracellular calcium to enter the cell. The rise in calcium concentration is transient, but it can be measured in situ by loading the cells with a calcium dependent fluorescent probe and monitored by the use of 96- or 384-well fluorescence plate readers. In the current assay, NIH 3T3/CCK$_2$R cells were seeded in black PolyLysin coated 384 well plates with clear bottom at 14000 cells per well and incubated overnight in 25 μl (per well) Gibco Nut. mix F-12 Glutamax medium with 10% FCS, 1% penicillin and streptomycin and 1 mg/ml genetin (G418). The next day 25 ml dye solution (Ca 5 probe from Molecular Devices, dissolved in HBSS/Hepes buffer pH 7.4 containing 0.1% Ovalbumin, 0.005% Tween 20, 3.5 μM Probenecid, 50 μM PDE inhibitor and 0.2% CaCl$_2$) was added per well and the plate was incubated for 1 hour at room temperature. After incubation, these plates were loaded onto FLIPR Tetra from Molecular Devices together with the sample plates containing dilution series of gastrin analogues in HBSS/Hepes buffer with 30% DMSO. During the assay run, 1 μl sample was transferred from the sample plate to the assay plate. Beside the baseline fluorescence measurement, a second fluorescence measurement was performed after 30 seconds with both measurements using the filterset 540 nm/590 nm. For each agonist concentration E=Emax. Emin was calculated. The concentration-response relationship was calculated using a four-parameter logistic model using non linear regression analysis (Prism 5.02, GraphPad Software).

Assay (II): Minipig i.v. PK

Six male Göttingen mini-pigs weighing approximately 20 to 23 kg from Ellegaard Gottingen Minipigs A/S, Denmark were comprised in the study. The mini-pigs were dosed intra venous (i.v.) via a central catheter in vena cava caudalis. The catheter was flushed with 10 ml saline post administration.

Blood was sampled from the central catheter. Test substances were dissolved in a vehicle consisting of in 50 mM sodium phosphate, 145 nM sodium chloride, 0.05% tween80 pH 7.4. The pigs were dosed with 10 nmol of gastrin compound (such as gastrin derivative)/kg body weight or 10 nmol Gastrin-17/kg body weight. Blood samples were taken at the following time points: pre-dose, 5 minutes, 15 minutes, 30 minutes, 45 minutes, 1, 1.5, 2, 3, 4, 6, 8, 10, 24, 48, 72, 96, 120, 168, 192 and 216 hours post dosing. The blood samples were collected into test tubes containing EDTA buffer for stabilization and kept on ice for max. 20 minutes before centrifugation. The centrifugation procedure to separate plasma may be: 4° C., approx. 2500 g for 10 minutes. Plasma was collected and immediately transferred to Micronic tubes stored at −20° C. until assayed.

Blood samples were analysed for gastrin compound content using a competitive scintillation proximity assay (SPA). The assay is a radiometric-ligand binding assay using LEAD-SEEKER™ imaging particles. The assay involves a rabbit anti-human gastrin-17(2-17) polyclonal antibody, wherein the human gastrin-17(2-17) against which said antibody raised contained position 2-17 of SEQ ID NO:2 (said antibody is obtainable from professor Jens Rehfeld, Rigshospitalet, Copenhagen, Denmark), [$^{125}$I]-Tyr$^{12}$ gastrin I (human) (which has the sequence pGlu-Gly-Pro-Trp-Leu-Glu-Glu-Glu-Glu-Glu-Ala-[$^{125}$I]Tyr-Gly-Trp-Met-Asp-Phe-NH$_2$, item no. NEX176010UC, PERKINELMER® Waltham, Massachusetts, USA) and PS LEADSEEKER™ particles coated with anti-rabbit Ig antibodies. Gastrin compounds (in calibrators, controls or unknown samples) and [$^{125}$I]-Tyr12 human gastrin I will compete for the binding to the polyclonal rabbit anti human gastrin I antibody. The anti-rabbit Ig antibodies on the LEADSEEKERTM™ particles recognize the anti-gastrin antibodies bringing the [$^{125}$I-] gastrin molecules in close proximity to the LEADSEEKERTM™ particles resulting in light emission from the particles. The LEAD-SEEKERTM™ will image the emitted light that is reversely correlated to the amount of gastrin compound present in the sample. 5μL sample, calibrator or control was applied to white 384-well polystyrene plates followed by 10μantibody working solution (rabbit-anti-Gastrin serum from rabbit 2609 batch 11/10-73), 10μl tracer working solution and 10μl bead working solution. The plate was sealed and shaken 1 minute on a Micromix shaker. After incubation over night at room temperature the plate was centrifuged for 1 minute at 1000 rpm in an Eppendorf centrifuge 5810. After exchanging the seal against a new one, the light emission was detected with a LEADSEEKERTM™ Multimodality Imaging System. The used measuring time was 20 minutes.

The concentration-response relationship was calculated using a four-parameter logistic model using non linear regression analysis and the output of the assay was the concentration of the respective gastrin analogue in pM. The in vivo plasma half life was determined by non-compartmental analysis (NCA) of plasma concentration-time profiles from each animal. NCA may be carried out as follows: Plasma concentration-time profiles were analyzed by non-compartmental pharmacokinetics analysis (NCA) using WinNonlin (Pharsight Inc., Mountain View, Calif., USA); NCA was performed using the individual plasma concentration-time profiles from each animal.

The lower limit of detection for different gastrin compounds is shown in Table 1.

TABLE 1

The lower limit of detection for different gastrin compounds in Assay (II)

| Gastrin compound, wherein # is {2-(2-{2-[2-(2-{2-[4-Carboxy-4-(17-carboxyheptadecanoylamino)butyrylamino]ethoxy}-ethoxy)acetylamino]-ethoxy}ethoxy)acetyl} and gastrin-17 is as defined by SEQ ID NO: 2 | Lower limit of detection (pM) |
|---|---|
| gastrin-17 | 20 |
| N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}-Gastrin-17 | 70 |
| [Leu15]Gastrin-17 | 500 |
| N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}-[Leu15]Gastrin-17 | 5000 |

Assay (III): Rat i.v. PK 5 male Sprague Dawley rats weighing approximately 400-450 g from Taconic, Denmark are used in the study. The rats are dosed intra venous (i.v.) via an injection in the tail vein. Blood is sampled from tongue. Test substances are dissolved in a vehicle consisting of in 50 mM sodium phosphate, 145 nM sodium chloride, 0.05% tween80 pH 7.4. The rats are dosed with 6 nmol/kg body weight with gastrin derivative or Gastrin-17. Blood samples are taken at the following time points: pre-dose, 2 minutes, 15 minutes, 30 minutes, 1, 2, 4, 6, 24, 30, 48, 72, and 96 hours post dosing. The blood samples are collected into test tubes containing EDTA buffer for stabilization and kept on ice for max. 20 minutes before centrifugation. The centrifugation procedure to separate plasma may be: 4° C., approx. 2500 g for 10 minutes. Plasma is collected and immediately transferred to Micronic tubes stored at −20° C. until assayed.

Plasma samples are analysed for gastrin compound content using the Human Gastrin I ELISA kit "EIA-4187" from DRG Instruments GmbH, Germany. Instead of using kit standards, defined concentrations of the respective compounds in EDTA plasma are used as calibrators. Furthermore sample volume is 35 μl and not 100 μl as stated in the kit description. Samples are analysed undiluted or diluted in rat plasma. The limits of detection that have been achieved are listed in Table 2.

The concentration-response relationship is calculated using a four-parameter logistic model using non linear regression analysis and the output of the assay is the concentration of the respective gastrin analogue in pM. The in vivo plasma half life is determined by non-compartmental analysis (NCA) of plasma concentration-time profiles from each animal. NCA may be carried out as follows: Plasma concentration-time profiles are analyzed by non-compartmental pharmacokinetics analysis (NCA) using WinNonlin (Pharsight Inc., Mountain View, Calif., USA); NCA is performed using the individual plasma concentration-time profiles from each animal.

Example 9

In vitro receptor potency of gastrin compounds was measured using Assay (I). The results are shown in Table 2 and 3.

TABLE 2

Receptor potency of gastrin compounds.

| Gastrin compound, wherein # is {2-(2-{2-[2-(2-{2-[4-Carboxy-4-(17-carboxyheptadecanoylamino)butyrylamino]ethoxy}-ethoxy)acetylamino]-ethoxy}ethoxy)acetyl} and gastrin-17 is as defined by SEQ ID NO: 2 | N-terminal Acylation/ Truncation | Relative Receptor Potency |
|---|---|---|
| [Leu15] Gastrin-17 | none | 100 |
| N-α-#-[Leu15] Gastrin-17 | 1 | 76 |
| N-α-#-[Leu15] Gastrin-17 (2-17) | 2 | 51 |
| N-α-#-[Leu15] Gastrin-17 (3-17) | 3 | 71 |
| N-α-#-[Leu15] Gastrin-17 (4-17) | 4 | 58 |
| N-α-#-[Leu15] Gastrin-17 (5-17) | 5 | 59 |
| N-α-#-[Leu15] Gastrin-17 (6-17) | 6 | 68 |
| N-α-#-[Leu15] Gastrin-17 (7-17) | 7 | 39 |
| N-α-#-[Leu15] Gastrin-17 (8-17) | 8 | 49 |
| N-α-#-[Leu15] Gastrin-17 (9-17) | 9 | 30 |
| N-α-#-[Leu15] Gastrin-17 (10-17) | 10 | 32 |
| N-α-#-[Leu15] Gastrin-17 (11-17) | 11 | 13 |
| N-α-#-[Leu15] Gastrin-17 (12-17) | 12 | 7 |
| N-α-#-[Leu15] Gastrin-17 (13-17) | 13 | 6 |
| N-α-#-[Leu15] Gastrin-17 (14-17) | 14 | 0 |
| N-α-#-[Leu15] Gastrin-17 (15-17) | 15 | 0 |
| N-α-#-Gastrin-17 (16-17) | 16 | 0 |

TABLE 3

Receptor potency of gastrin compounds.

| Gastrin compound, wherein # is {2-(2-{2-[2-(2-{2-[4-Carboxy-4-(17-carboxyheptadecanoylamino)butyrylamino]ethoxy}-ethoxy)acetylamino]-ethoxy}ethoxy)acetyl} and gastrin-17 is as defined by SEQ ID NO: 2 | Acylation Position | Relative Receptor Potency |
|---|---|---|
| [Leu 15] Gastrin-17 | none | 100 |
| N-α-#-[Leu15] Gastrin-17 | N-terminal | 57 |
| [Lys2(N-ε-#), Leu15] Gastrin-17 | Lys-2 | 48 |
| [Lys3(N-ε-#), Leu15] Gastrin-17 | Lys-3 | 60 |
| [Lys4(N-ε-#), Leu15] Gastrin-17 | Lys-4 | 30 |
| [Lys5(N-ε-#), Leu15] Gastrin-17 | Lys-5 | 42 |
| [Lys6(N-ε-#), Leu15] Gastrin-17 | Lys-6 | 40 |
| [Lys7(N-ε-#), Leu15] Gastrin-17 | Lys-7 | 34 |
| [Lys8(N-ε-#), Leu15] Gastrin-17 | Lys-8 | 32 |
| [Lys9(N-ε-#), Leu15] Gastrin-17 | Lys-9 | 19 |
| [Lys10(N-ε-#), Leu 15] Gastrin-17 | Lys-10 | 19 |
| [Lys11(N-ε-#), Leu 15] Gastrin-17 | Lys-11 | 15 |
| [Lys12(N-ε-#), Leu 15] Gastrin-17 | Lys-12 | 6 |
| [Lys13(N-ε-#), Leu 15] Gastrin-17 | Lys-13 | 5 |
| [Lys14(N-ε-#), Leu 15] Gastrin-17 | Lys-14 | 0 |
| [Lys15(N-ε-#)] Gastrin-17 | Lys-15 | 0 |
| [Lys16(N-ε-#), Leu 15] Gastrin-17 | Lys-16 | 0 |
| [Lys17(N-ε-#), Leu 15] Gastrin-17 | Lys-17 | 0 |

Example 10

Minipig i.v. PK

Half life of gastrin compounds was determined according to Assay (II). The results are shown in Table 4.

TABLE 4

Half life (t½) of gastrin compounds, which consist of a gastrin sequence and a derivatisation group as specified in the table. Gastrin-17 is as defined by SEQ ID NO: 2. # is {2-(2-{2-[2-(2-{2-[4-Carboxy-4-(17-carboxyheptadecanoylamino)butyrylamino]ethoxy}ethoxy)-acetylamino]-ethoxy}ethoxy)acetyl}.

| Gastrin sequence | Derivatisation group | t½ ± SD (h) |
|---|---|---|
| gastrin-17 | none | 0.058 ± 0.007 |
| gastrin-17 | N-alpha-#- | 64 ± 6 |
| [Leu15] gastrin-17 | N-alpha-#- | 109 ± 26 |
| [Leu15] gastrin-17(4-17) | N-alpha-#- | 95 |
| [Leu15] gastrin-17(7-17) | N-alpha-#- | ~95 |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A gastrin derivative comprising:
    gastrin-17 or an analogue thereof, wherein the analogue is selected from the group consisting of [Leu15] gastrin-17, [Lys3, Leu15] gastrin-17, [Lys8, Leu15] gastrin-17, and [Lys14, Leu15] gastrin-17; and
    a derivatisation group comprising a $C_{12-22}$ acyl group, wherein said derivatisation group is {2-(2-{2-[2-(2-{2-[4-Carboxy-4-(17-carboxyheptadecanoylamino)butyrylamino]ethoxy}-ethoxy)acetylamino]-ethoxy}ethoxy)acetyl}, and wherein said derivatisation group is attached to a position selected from the group consisting of the N-terminal amino group, position 3, 8, and 14 of gastrin-17 or an analogue thereof.

2. The gastrin derivative of claim 1, wherein said gastrin derivative is N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl}gastrin- 17.

3. The gastrin derivative of claim 1, wherein said gastrin derivative is N-alpha-{2-(2-{2-[2-(2-{2-[4-Carboxy-4-(17-carboxyheptadecanoylamino)butyrylamino]ethoxy}-ethoxy)acetylamino]-ethoxy}ethoxy)acetyl} [Leu15] gastrin-17 (1-17).

* * * * *

SEQUENCE LISTING

```
<160> NUMBER OF SEQ ID NOS: 3

<210> SEQ ID NO 1
<211> LENGTH: 34
<212> TYPE: PRT
<213> ORGANISM: Artificial
<220> FEATURE:
<223> OTHER INFORMATION: Based on human gastrin-34
<220> FEATURE:
<221> NAME/KEY: MISC_FEATURE
<222> LOCATION: (34)..(34)
<223> OTHER INFORMATION: THIS POSITION IS PHENYLALANINE AMIDE
```

```
<400> SEQUENCE: 1

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
                20                  25                  30

Asp Phe

<210> SEQ ID NO 2
<211> LENGTH: 17
<212> TYPE: PRT
<213> ORGANISM: Artificial
<220> FEATURE:
<223> OTHER INFORMATION: Based on human gastrin-17
<220> FEATURE:
<221> NAME/KEY: MISC_FEATURE
<222> LOCATION: (17)..(17)
<223> OTHER INFORMATION: THIS POSITION IS PHENYLALANINE AMIDE

<400> SEQUENCE: 2

Gln Gly Pro Trp Leu Glu Glu Glu Glu Ala Tyr Gly Trp Met Asp
1               5                   10                  15

Phe

<210> SEQ ID NO 3
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: THIS POSITION IS PHENYLALANINE AMIDE

<400> SEQUENCE: 3

Trp Leu Glu Glu Glu Glu Glu Ala Tyr Gly Trp Met Asp Phe
1               5                   10
```